United States Patent [19]

Woiszwillo et al.

[11] Patent Number: 5,599,719

[45] Date of Patent: *Feb. 4, 1997

[54] METHOD FOR ISOLATING BIOMOLECULES FROM A BIOLOGICAL SAMPLE WITH LINEAR POLYMERS

[75] Inventors: James E. Woiszwillo, Milford, Mass.; Fred Rothstein, Long Beach, Calif.

[73] Assignee: Middlesex Sciences, Inc., Norwood, Mass.

[*] Notice: The term of this patent shall not extend beyond the expiration date of Pat. No. 5,525,519.

[21] Appl. No.: 107,822

[22] PCT Filed: Jan. 7, 1993

[86] PCT No.: PCT/US93/00073

§ 371 Date: Aug. 26, 1993

§ 102(e) Date: Aug. 26, 1993

[87] PCT Pub. No.: WO93/03639

PCT Pub. Date: Mar. 4, 1993

Related U.S. Application Data

[63] Continuation-in-part of Ser. No. 817,610, Jan. 7, 1992, Pat. No. 5,525,519.

[51] Int. Cl.$^6$ .................................................. G01N 33/487
[52] U.S. Cl. .............................. 436/88; 436/17; 436/513; 436/539; 436/503
[58] Field of Search ............................... 436/17, 88, 503, 436/512, 513, 539, 546, 815

[56] References Cited

U.S. PATENT DOCUMENTS

| | | | |
|---|---|---|---|
| Re. 31,268 | 6/1983 | Hansen | 260/112 B |
| 3,631,018 | 12/1971 | Shanbroom et al. | 260/112 |
| 3,652,530 | 3/1972 | Johnson et al. | 260/112 B |
| 3,790,552 | 2/1974 | Johnson et al. | 260/112 B |
| 3,869,436 | 3/1975 | Falksveden et al. | 260/112 B |
| 3,897,414 | 7/1975 | Albertsson | 536/25.41 |
| 4,016,039 | 4/1977 | Schreiber | 195/66 R |
| 4,093,606 | 6/1978 | Coval | 260/112 B |
| 4,115,375 | 9/1978 | Pederson | 260/112 R |
| 4,124,576 | 11/1978 | Coval | 260/112 B |
| 4,164,495 | 8/1979 | Hansen | 260/112 B |
| 4,165,370 | 8/1979 | Coval | 424/85 |
| 4,543,210 | 9/1985 | Mitra et al. | 260/112 B |
| 4,578,218 | 3/1986 | Saundry et al. | 260/112 B |
| 4,683,294 | 7/1987 | Van Wijnendaele et al. | 530/371 |
| 4,692,331 | 9/1987 | Uemura et al. | 424/85 |
| 4,740,304 | 4/1988 | Tjerneld et al. | 210/639 |
| 4,822,535 | 4/1989 | Ekman et al. | 264/4.3 |
| 4,874,708 | 10/1989 | Makula et al. | 435/272 |
| 4,910,182 | 3/1990 | Hums et al. | 502/402 |
| 5,135,875 | 8/1992 | Meucci et al. | 436/518 |
| 5,177,194 | 1/1993 | Sarno et al. | 530/412 |
| 5,288,853 | 2/1994 | Bhattacharva et al. | 530/383 |

FOREIGN PATENT DOCUMENTS

| | | |
|---|---|---|
| 1064396 | 10/1979 | Canada . |
| 2512735 | 9/1976 | Germany . |
| 3430320 | 3/1985 | Germany . |
| 3625266 | 2/1987 | Germany . |
| 1109170 | 8/1984 | U.S.S.R. . |
| WO90/03164 | 9/1989 | WIPO . |

OTHER PUBLICATIONS

Albertsson et al., "Seperation of Membrane Components by Partition in Detergent–Containing Polymer Phase System", J. of Chromatography, 215, 1981, pp. 131–141.

Hammar, L. et al., "The Use of Aqueous Two–Phase Systems to Concentrate and Purify Bovine Leukemia Virius Outer Envolope Protein g p51," Biotech and Appl. Biochem, Nov., 1986, pp. 296–306.

Green et al., "Protein Fractionation on the Basis of Solubility in Aqueous Solutions of Solk and Organic Solvents", Methods in Enzymology, Ed. C. Kaplan, 1, 99–121, 1955.

Ingham, "Precipitation of Proteins with Polyethylene Glycel" Methods in Enzymology, vol. 182, 301–306, 1990.

Polson et al., "The Fractionation of Protein Mixtures by Linear Polymers of High Molecular Weight", Biochim. ET Biophys. Acta, 82, 463–475, 1964.

Hasko et al., "Fractionation of Plasma Proteins with PEG" Hoematoligia, 14(2), pp. 199–206, 1981.

Farrugia et al., "Studies on the Prowrement of Coagulation Factor VIII: Selective Precipitation of Factor VII with Hydrophilic Polymers, " Thromb Horm., 51(3)338–342, 1984.

Spence et al., "Use of Water–Soluble Polymers in the Precipitation of Ikod Group Diagnostic Reagents", Med. Lab. Sciences, 42, 115–117, 1985.

Wiesen et al., "Gel Difusion Reactions and Biological Properties of Paeonia Tammin," Phytopath. 2, 93, 56–68, 1978.

Virella et al., "Isolation of Soluble Immune Compleros from Human Serum: Combined Use of PEG Preciptation, Gel Filtration . . . ", Methods in Enzymology, 74, 644–663, 1981.

Clamagirand, C., et al., "Partial Purification and Functional Properties of an Endoprotease from Bovine Neurosecretory Granules Cleaving Proocytocin/Neurophysin Peptides at the Basic Amino Acid Doublet," Biochemistry, 26(19): 6018–6023 (1987).

Feldman, J. A., et al., "Semiinterpenetrating Networks Based on Triazine Thermoset and N–Alkylamide Thermoplastics," Am. Chem. Soc. Symposia Series, 367: 244–268 (1988).

Georgiou, M., et al., "Functional and Physical Characteristics of Rat Leydig Cell Populations Isolated by Metrizamide and Percoll Gradient Centrifugation," Biology of Reproduction, 37: 335–341 (1987).

(List continued on next page.)

Primary Examiner—Donald E. Czaja
Assistant Examiner—Milton I. Cano
Attorney, Agent, or Firm—Jones & Askew

[57] ABSTRACT

A method, composition, and kit for isolating biomolecules from a biological sample wherein the sample is mixed with a soluble, linear polymer, such as polyvinylpyrrolidone, to form a precipitate. The biomolecule of interest is found in the precipitate or is isolated from the supernatant.

11 Claims, No Drawings

OTHER PUBLICATIONS

He, D., et al., "Mast–Cell Heterogeneity; Functional Comparison of Purified Mouse Cutaneous and Peritoneal Mast Cells," *The Society for Investigative Dermatology, Inc.*, 95(2) (1990).

Heuck, C. C., et al., "Rapid Development of Immunoprecipitins in Agarose Gel," *Clinica Chimica Acta*, 98:195–199 (1979).

Ralston, G. B., "Effects of 'Crowding' in Protein Solutions," *J. Chemical Education*, 67(10) Oct. 1990, pp. 857–860.

Sanbar, et al., "Hypolipidemic Effect of Polyvinylpyrrolidone in Man," *Circulation*, 38: 771–776 (1968).

Schultze, H. E., et al., "Molecular Biology of Human Proteins—With Special Reference to Plasma Proteins," 1: 240–317 (1966).

Sperling, L. H., "Interpenetrating Polymer Networks and Related Materials," *Plenum Press*, New York (1981).

Strong, M. J., et al., "Isolation of Fetal Mouse Motor Neurons on Discontinuous Percoll Density Gradients," *In Vitro Cellular & Developmental Biology*, 25(10): 939–945 (1989).

van Suylichen, et al., "The Efficacy of Density Gradients for Islet Purification: A Comparison of Seven Density Gradients," *Transplant International*, 3: 156–161 (1990).

Zeppezauer, et al., "Protein precipitation by uncharged water–soluble polymers," *Biochim. Biophys. Acta*, 94: 581–583 (1965).

METHOD FOR ISOLATING BIOMOLECULES FROM A BIOLOGICAL SAMPLE WITH LINEAR POLYMERS

This is a continuation-in-part of U.S. patent application Ser. No. 07/817,610 filed Jan. 7, 1992, now U.S. Pat. No. 5,525,519.

BACKGROUND OF THE INVENTION

Protein Isolation

Protein isolation is an important tool in biological research, clinical diagnostics and the production of pharmaceuticals, especially production by recombinant techniques. The scientific researcher must obtain a protein quickly while retaining high specific activity; the clinician must identify proteins in biological samples in order to make an accurate diagnosis; and the molecular biologist must recover and purify large quantities of proteins produced by recombinant organisms.

Scientists have traditionally isolated proteins by precipitating them from biological samples with salts, such as ammonium sulfate, or organic solvents, such as ethanol. Exposure to the chemicals used in such methods often causes protein denaturation. In addition, separation of the proteins from the precipitating chemical is difficult and may cause further denaturation.

The ammonium sulfate precipitation technique, also known as "salting out," is based on the fact that the solubility of most proteins decreases at high electrolyte concentration. Sulfate is used because multivalent ions are more effective than monovalent ions. This procedure is usually carried out in the cold (0°–4° C.) with control of pH close to neutrality. Different classes of proteins precipitate depending on the concentration of salt added. The disadvantage to this method is the difficulty of removing residual salt from the precipitate or supernatant. Often dialysis is used, but is very time consuming.

Organic solvents are often used for fractional precipitation of proteins. However, there is a risk that the solvent will denature the protein unless kept at a temperature near the freezing point. In addition, the solvent must be removed from the protein. A solvent such as ethanol is generally removed by lyophilizing the precipitated proteins.

Recent advances in protein purification have centered around the development of high performance ion exchange, affinity chromatography, hydrophobic interactions and gel filtration chromatography. The biological sample is loaded onto a chromatography column and is eluted with the appropriate solvent into fractions that are analyzed for protein activity. This method is expensive, time consuming, and poorly suited for large scale protein purification.

Many scientist continue to use traditional methods alone or in combination with the recently developed chromatography procedures. For example, after precipitation of a protein from a biological sample with ammonium sulfate, protein is separated from the ammonium sulfate salt by chromatography. Often the protein loses activity or becomes denatured during one or more steps of the procedure, resulting in a low yield or inaccurate identification.

Polymer Studies

In the mid 1960's, Polson et al., *Biochim. Biophys. Acta* 82:463–475 (1964), analyzed a variety of high molecular weight polymers for purifying proteins including polyethylene glycol (PEG), dextran, nonylphenol-ethoxylates (NPEs), polyvinyl alcohol (PVA) and polyvinylpyrrolidone (PVP). Polson et al. concluded that PEG is the most suitable of the tested polymers for protein precipitation. The disadvantage to PEG is that it must be removed from the protein either by passage through a DEAE or cellulose column under conditions that adsorb the proteins and wash out the PEG with the effluent or by adding ethanol to precipitate the proteins from the supernatant, leaving the PEG in the supernatant. Polson et al. explicitly caution against the use of PVE, PVP and NPEs because of their high intrinsic viscosities and because, according to their observations, the polymers cause significant protein denaturation. The results of Polson et al. were confirmed and extended by Zeppezauer and Brishammar, *Biochim. Biophys.* Acta 94:581–583 (1965) who precipitated kidney proteins with three high molecular weight preparations of Polyox™, a PEG resin obtained from Union Carbide Corp. (Danbury, Conn).

Polyethylene glycol (PEG), also known as poly(oxyethylene) glycol, is a condensation polymer of ethylene oxide and water having the general chemical formula $HO(CH_2CH_2O)_nH$. PEG is used as a water-soluble lubricant for rubber, textile and metal manufacture; in food, cosmetics, water paints, paper coatings, and polishes; and as an ointment base in pharmaceuticals.

Dextran is a term applied to polysaccharides produced by bacteria growing on a sucrose substrate. Native dextrans produced by bacteria such as *Leuconostoc mesenteroides* and *Lactobacteria dextranicum* usually have a high molecular weight. The lower molecular weight dextrans used as plasma volume expanders or blood flow adjuvants are usually prepared by depolymerization of native dextrans or by synthesis.

NPEs are a class of long chained compounds often used as surfactants. They are usually derivatized to meet the desired solubility requirements.

PVA is a polymer prepared from polyvinyl acetates by replacement of the acetate groups with hydroxyl groups and has the formula $(CH_2CHOH)_n$. Most polyvinyl alcohols are soluble in water and are used as elastomers in the plastics industry, as viscosity increasing agents in the pharmaceutical industry, and as ophthalmic lubricants.

PVP is a non-ionogenic, hydrophilic polymer having a mean molecular weight ranging from approximately 10,000 to 700,000 and the chemical formula $(C_6H_9NO)_n$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan, and Vinisil™. PVP is non-toxic, highly hygroscopic and readily dissolves in water or organic solvents. PVP has a wide variety of uses such as in pharmaceuticals, as a complexing agent, and for the detoxification of chemicals. It is also used in tableting, photographic emulsions, cosmetics, detergents, adhesives, and beer and wine clarification. PVP was used as a blood plasma expander during World War II, but when high molecular weights were found to be adsorbed in tissues this use was abandoned. Intravenous PVP has been used to decrease human serum lipids as described by Sanbar and Smet, *Circulation* 38:771–776 (1968).

PEG, dextran, PVA and PVP are commercially available from chemical suppliers such as the Sigma Chemical Company (St. Louis, Mo.). NPEs require custom synthesis and can be ordered from special chemical producers.

Recombinant Techniques

Many proteins, such as for example, human growth hormone and insulin, are now produced by recombinant techniques. The gene encoding the protein is inserted into a bacterial or viral vector causing production of large quantities of the protein which must then be isolated from the other proteins in the growth media, or fermentation fluid. A rapid, inexpensive method for the purification of proteins produced by recombinant techniques would help reduce the costs and improve the recovery of proteins produced in this manner.

Drug Disposition

A sufficient amount of pharmaceutical agent or drug must reach its site of action in order to exert a desired effect. Drug absorbed into the blood from the site of administration often binds to proteins, such as albumin, that retard the delivery of drug to the site of action. A drug having a higher affinity for serum proteins will require a larger dose to achieve the desired effect.

During pharmaceutical development, drug disposition studies are performed to determine the amount of drug bound to serum protein. After administration of drug, serum proteins are isolated by chromatography or are precipitated by chemicals such as ammonium sulfate. The concentration of the drug in the protein fraction is determined and is compared with the total concentration of drug found in the intact sample through analytical techniques. These methods are time consuming and do not provide sufficient information concerning the identity of the proteins to which the drug is bound.

Urine samples are also analyzed for drug or drug metabolite concentration to ensure that the drug is excreted and is not retained by the body. Interfering proteins are often separated from drug as described above using time consuming procedures.

Albumin Isolation

Albumin is a simple protein distributed throughout the tissues and fluids of plants and animals, well known for its presence in the white portion of poultry eggs. Albumin is soluble in water and is easily denatured by heat, acid or neutral solutions. Bovine serum albumin (BSA) is derived from bovine blood and is often used in in vitro biological studies. Normal human serum albumin is obtained by fractionating blood plasma proteins from healthy persons and is used as a transfusion material. Serum albumin is also used in diagnostics such as, for example, the use of radioiodinated serum albumin in determining blood volume and cardiac output. Therefore, there is a great need for an inexpensive method of producing large quantities of purified albumin.

Immunoglobulin Isolation

The immunoglobulins IgG, IgM, IgA, IgE and IgD, which are found in the gamma globulin fraction of vertebrate serum proteins, constitute the circulating antibody population and provide the humoral immune response necessary to fight infection and disease. A measurement of the serum globulin to albumin ratio provides a good indication of the presence of an immune response to infection and an individual's ability to combat the infection. An abnormally high concentration of globulin in the serum is often an indication of a hyperproliferative disorder such as myeloma or Bence Jones proteins. Purified immunoglobulins are necessary for scientific research, especially in the development of vaccines, and for passive immunization of individuals who have been recently exposed to a bacteria or virus for which a vaccine is not yet available. Therefore, a rapid method for isolating immunoglobulins from blood for research, diagnostic or therapeutic purposes is necessary.

Antibodies

Monoclonal antibodies are created by fusing a normal antibody-producing lymphocyte from the spleen of a recently immunized experimental animal to a myeloma cell line to form a hybridoma. The myeloma cell causes the continuous production of the antibody of interest which is usually recovered from ascites fluid. Monoclonal antibodies must be isolated from the other proteins present in the ascites fluid before use as reagents in diagnostic kits, scientific research, or coupled to a drug to provide a "magic bullet" that is directed to a target site such as a malignant tumor. Polyclonal antibodies are produced by injecting an animal, such as a mouse, rat or rabbit, with an antigen, collecting blood, and isolating the immunoglobulin fraction that binds to the antigen, usually by passage of the immunoglobulin fraction through an affinity column to which antigen has been immobilized. The resulting polyclonal antibodies are used for the same purposes as monoclonal antibodies described above except that the specificity of a polyclonal antibody for a particular antigen is not as great. An inexpensive, rapid method of isolating and purifying monoclonal or polyclonal antibodies would greatly simplify antibody production.

Spinal Fluid and Urine Analysis

Medical diagnosis of disease or disorders is often achieved by analyzing bodily fluids such as spinal fluid or urine. Separation of biomolecules from interfering substances in the spinal fluid or urine sample would provide a faster, more reliable diagnosis.

What is needed is a biomolecule isolation method that is simple, inexpensive and fast, yet allows for the isolation of a relatively pure, active biomolecule.

It is therefore an object of the present invention to provide a non-denaturing method of isolating a biomolecule.

It is a further object of the present invention to provide a rapid, reproducible method of isolating a relatively pure protein.

It is a further object of the present invention to provide a method of isolating a biomolecule from a biological sample in a single step.

It is a further object of the present invention to provide a method of isolating large quantities of relatively pure protein.

It is a further object of the present invention to provide a method of determining the globulin to albumin ratio in serum.

It is a further object of the present invention to provide a method of determining the disposition of a drug in serum proteins.

SUMMARY OF THE INVENTION

A method, composition, and kit for the isolation of an active biomolecule, such as a protein, from a biological sample are provided. A soluble, linear polymer is added to the sample to form a precipitate. The biomolecule of interest is isolated from either the precipitate or the supernatant. Biomolecules of interest are isolated from the supernatant by subsequent polymer precipitation or precipitation with a zinc compound. The addition of a biological detergent that solubilizes protein complexes to the sample prior to precipitation with the polymer will increase the degree of precipitation.

Isolation of any particular biomolecule depends on the pH of the sample before, during or after addition of the polymer. The sample is adjusted to a predetermined pH before or after polymer addition with an acid or base, preferably with one or more low molecular weight moieties containing a carboxyl or amino group, such as imidazole, amino caproic acid, an amino acid or a mixture thereof. Alternatively, the pH of the linear polymer is adjusted and the pH-adjusted polymer is added to the sample to cause precipitation and selective biomolecule isolation in a single step. The preferred concentration of low molecular weight moiety used for the pH adjustment is dependent on the pH desired for the isolation procedure.

Preferably, the polymer is an aqueous solution of polyvinylpyrrolidone (PVP). Alternatively, the polymer is a mixture of polyvinylpyrrolidone and one or more additional soluble, linear polymers, such as polyethylene glycol, dextran, nonylphenol ethoxylates or polyvinyl alcohol, most preferably a mixture of polyvinylpyrrolidone (PVP) and polyethylene glycol (PEG).

Preferably, precipitation of the biomolecule from the biological sample takes place at room temperature or at a temperature below room temperature, such as a temperature between 2° C. and 20° C. Most preferably, precipitation occurs at a temperature at which the polymer or mixture of polymers is viscous, such as at 4° C.

In the preferred method, immunoglobulins are isolated from a biological sample such as blood serum by first adjusting the pH of a polymer solution of polyvinylpyrrolidone and polyethylene glycol to a neutral pH. The pH is adjusted with a mixture of imidazole and amino caproic acid. Alternatively, the pH is adjusted with an amino acid solution containing glutamic acid, histidine, and lysine. A solution containing a biological detergent, such as a polyoxyethylenesorbitan, most preferably polyoxyethylenesorbitan monolaurate is added to the sample, and then the polymer solution is added to the sample to precipitate a relatively pure immunoglobulin fraction, leaving interfering proteins, such as albumin, and other substances in the supernatant. Preferably, the precipitated gammaglobulin is resuspended in an alkaline solution such as glycerol and imidazole, glycerol and sodium bicarbonate, imidazole, or a salt solution such as Trizma™ base (tris[hydroxymethyl]-aminomethane), for enhanced solubility and stability.

In an alternative preferred method, proteins are precipitated from a urine or spinal fluid sample by first adjusting the pH of a polymer solution of polyvinylpyrrolidone and polyethylene glycol to a neutral pH with a glycine solution, preferably a solution of zinc glycinate, and then combining the polymer solution with the sample.

A method for the disposition of a drug in serum proteins is also described by isolating the globulin fraction, precipitating albumin from the supernatant, and then measuring the amount of a drug in each fraction.

A method is also provided for determining the globulin to albumin ratio in serum samples for diagnostic purposes by isolating the globulin and albumin as described above and then determining the concentration of each and their ratio in the sample.

DETAILED DESCRIPTION OF THE INVENTION

A method, composition, and kit are provided for the isolation of a biologically active biomolecule from a biological sample with linear polymers. Biomolecules to be isolated include proteins, lipids, nucleic acids, carbohydrates, and non-protein hormones. It will be understood by those skilled in the art that the isolated biomolecule could also be a targeted molecule such as a drug.

The biomolecule of interest is isolated by adding a sufficient amount of a soluble, linear polymer, or mixture of polymers, to the biological sample to form a precipitate. The biomolecule is then isolated from either the precipitate or supernatant by decantation or subsequent precipitation.

Selection of a particular biomolecule of interest from other biomolecules and interfering substances in the sample is achieved by adjusting the pH of the sample to a predetermined value either before, after, or during addition of the polymer. Preferably, the sample is adjusted to a predetermined pH between 4 and 9.2 by adding a pH-adjusted polymer solution to the sample to allow pH adjustment, precipitation and isolation of the desired biomolecule in a single step. The pH of the polymer solution is adjusted by the addition of an acid or base, preferably a low molecular weight moiety containing a carboxyl or amino group such as imidazole, caproic acid, an amino acid or a mixture thereof that results in minimal salt formation. Alternatively, the sample is adjusted, either before or after addition of the polymer, by adding the acid, base, or low molecular weight moiety solution directly to the sample.

Isolation of a biomolecule of interest from the resulting supernatant is achieved by adding a second polymer solution having a different mixture of polymers or a different pH, or by adding a zinc compound such as zinc sulfate to precipitate the biomolecule of interest from the supernatant.

Preferably, a biological detergent that solubilizes protein complexes, such as polyoxyethylenesorbitan, a polyoxyethylene ether such as 23 lauryl ether (known commercially as Brig 35™) or a Triton™ surfactant (preferably Triton X-102™), or sodium dodecyl sulfate (SDS), is added to the sample prior to the addition of the polymer solution to increase the yield and purity of precipitate. The preferred detergent is a polyxoyethylenesorbitan, most preferably polyxoyethylenesorbitan monolaurate available commercially as Tween-20™ from Sigma Chemical Company, St. Louis, Mo. The 23 lauryl ether (Brij 35™), Triton X-102™, and sodium dodecyl sulfate are also available from Sigma Chemical Company. Other commercially available biological detergents useful for solubilizing protein complexes include, for example, but are not limited to, the anionic biological detergents caprylic acid, cholic acid 1-decanesulfonic acid, deoxycholic acid, glycocholic acid, glycodeoxycholic acid, lauryl sulfate, taurocholic acid, and taurodeoxycholic acid; the cationic biological detergents cetylpyridinium chloride, dodecyltrimethylammonium bromide, hexadecyltrimethylammonium bromide, and tetradecyltrimethylammonium bromide; the zwitterionic (amphoteric) biological detergents (3 -[3-cholamidopropyldimethylammonio]-1-propanesulfonate (CHAPS) and (3-[3-cholamidopropyldimethylammonio]-2-hydroxy-1propanesulfonate) (CHAPSO); and the nonionic biological detergents n-decyl beta-D-glucopyranoside, digitonin™ (digitin), n-dodecyl beta-D-glucopyranoside, n-dodecyl beta-D-maltoside, n-heptyl beta-D-glucopyranoside, n-octyl alpha-D-glucopyranoside, n-octyl alpha-D-glucopyranoside, nonidet P-40™, n-nonyl beta-D-glucopyranoside and Triton X-100™. These biological detergents are also available from Sigma Chemical Company.

The preferred concentration of detergent is between approximately 0.5 and 5.0%. Preferably, equal volumes of the detergent solution and sample are combined and incubated for a sufficient amount of time to allow solubilization of protein complexes contained in the sample. An incubation time of five to thirty minutes at room temperature is generally sufficient.

Preferably, precipitation of the biomolecule from the biological sample takes place at room temperature (20° C.) or at a temperature below room temperature. Most preferably, precipitation occurs at a temperature at which the polymer or mixture of polymers is viscous. For example, a polymer mixture of PVP and PEG is slightly viscous at 4° C. It will be understood by those skilled in the art that the temperature should not be below the freezing point of the polymer or polymer mixture. Therefore, the polymer or polymer mixture should be maintained and the precipitation reaction conducted at a temperature between the freezing point of the polymer or polymer mixture and room temperature, most preferably at 4° C.

Polymers Used to Precipitate Biomolecules

The biomolecule is isolated by adding a sufficient amount of a water soluble, linear polymer such as polyethylene glycol (PEG), dextran, nonylphenol-ethoxylates (NPEs), polyvinyl alcohol (PVE), polyvinylpyrrolidone (PVP), or a mixture thereof, to form a precipitate. Preferably, the polymer is an aqueous solution of PVP having a molecular weight between 10,000 and 360,000, most preferably 40,000. PVP is dissolved in water in a concentration between 1 and 30 g/100 ml depending on the molecular weight of the polymer. Most preferably 20 g/100 ml of a 40,000 molecular weight (MW) solution of PVP is used. The volume of polymer added to the sample varies depending on whether the biomolecule of interest is to be retained in the supernatant or precipitated.

Polymer Networks

The soluble, linear polymer is added as a sole polymer, as a mixture of two or more polymers, or in a polymer network. A polymer network is a non-covalent linkage of polymers in a homogenous, insoluble, cross-linked or honeycomb-like structure that does not interfere with the water-binding properties of the linked polymers. Polymer networks are described in detail by Sperling, L. H. in the book entitled "Interpenetrating Polymer Networks and Related Networks" Plenum Press, N.Y., 1981, the teachings of which are incorporated herein. An aromatic dicyanine compound, such as 4,4-bisphenol A dicyanate, or a mixture of dicyanate and cyanate compounds, as described by Feldman and Huang in Am. Chem. Soc. Symposia Series, 367:244–268 (1988), which is incorporated by reference herein, provide suitable reagents for networking the polymers.

Preferably, two volumes of a dicyanate compound is combined with one volume of a polymer or polymer mixture to create the network. When the mixture is heated above the melting temperature of the dicyanate, the dicyanate esters undergo a cyclotrimerization reaction forming triazine rings and a relatively open network which immobilizes the polymer molecules. Preferably, the mixture is heated to a temperature between 80° C. and 90° C. for approximately 40 minutes. The resulting cross-linked structure remains thermally and mechanically stable and provides a homogenous mixture of water-absorbing polymers.

The network of polymers is preferably added to a sample as a sponge or honeycomb-like structure to rapidly isolate the biomolecule of interest. The polymers dispersed in the network absorb water in the sample, causing precipitation. The polymer network is then removed from the sample. The biomolecule of interest is isolated from the precipitate or eluted from the polymer network with a suitable solvent, such as water.

Adjustment of pH

The pH of the polymer or sample is preferably adjusted to a predetermined pH between 4 and 9.2 with an acid or base solution having a pH between 2 and 10.5. The acid or base solution is added to the polymer solution that is subsequently added to the sample, or the acid or base solution is added directly to the sample either before or after addition of the polymer.

Preferably, the acid or base solution contains a low molecular weight moiety possessing a charged carboxyl group or charged amino group. For example, the acid or base solution can contain imidazole, amino caproic acid, one or more amino acids or a small molecular weight silane basic silane compound that will preferably avoid the formation of salts. Most preferably, the acid or base solution contains imidazole or amino caproic acid. Such compounds are less costly than amino acids. Alternatively, the pH is adjusted with a solution containing a charged amino acid, such as aspartic acid, glutamic acid, lysine, arginine, histidine or salts thereof; an uncharged polar amino acid such as glycine, serine, threonine, cysteine, tyrosine, asparagine, or glutamine or salts thereof; or a mixture of charged and uncharged polar amino acids such as a mixture of glycine, cysteine, and lysine, or salts thereof, to achieve the desired pH.

The optimal pH is determined by establishing a sample pH gradient with the appropriate acid or base mixture by adding various pH-adjusted polymers to the sample or adding polymer to aliquots of the sample adjusted to various pHs, and analyzing the resulting supernatant or precipitate by conventional means such as gel electrophoresis, immunoblot, or enzyme-linked immunosorbant assay (ELISA) to determine which pH provides the greatest amount of the biomolecule of interest at the highest level of purity.

Ratio of Polymer to Sample

A sufficient amount of the polymer is added to a biological sample to either precipitate the biomolecule of interest or precipitate interfering biomolecule and other substances, leaving the biomolecule of interest in the supernatant. A polymer to sample volume ratio of from 1:1 to 20:1 will provide optimal separation. Preferably, the ratio of polymer to sample volume is 2:1.

The amount of polymer needed depends on the amount of water present in the sample. Samples containing larger quantities of water, such as urine, will require more polymer than more concentrated samples, such as blood serum.

Isolation of Proteins

It is believed that the combination of PVP and PEG successfully separate proteins by absorbing water from the sample by two different mechanisms. PVP binds water through its peptide bonds while PEG binds water through its hydroxyl groups. It is believed that these combined absorption mechanisms create a pure separation of proteins unknown in currently available protein purification and isolation methods.

Isolation of Immunoglobulins

For example, the method described herein is applied to the isolation of one or more proteins as follows: An immunoglobulin is isolated from a human blood serum sample with an aqueous polymer mixture of PVP and PEG, the PEG having a molecular weight range between 200 and 35,000. PVP having a molecular weight of 40,000 and PEG having a molecular weight of 3500 is preferred. Preferably, the PVP is dissolved in water and PEG is added to the aqueous PEG solution. The concentration of each polymer is preferably between 1 and 30 g/100 ml, most preferably 20 g/100 ml or 20%, for PEG having a molecular weight of 3500. Equal concentrations of PVP and PEG generally provide the most favorable isolation of protein.

The polymer solution is adjusted to a neutral pH between 6.8 and 7.2 with an acid or base solution prior to addition of the polymer solution to the sample. Preferably, the pH of the polymer solution is adjusted with a solution containing approximately 2.0% 6-amino caproic acid and 2 mg/ml imidazole. Alternatively, the pH is adjusted with an aqueous solution of approximately 1.2 mg/ml ascorbic acid, approximately 1.5 mg/ml histidine, and approximately 1.5 mg/ml lysine.

Approximately 2 volumes of the pH-adjusted PVP/PEG polymer mixture is added to one volume of blood serum to form a precipitate. Most preferably, 1 ml of polymer is added to 0.5 ml of serum. Preferably, the polymer mixture added to the blood is viscous. Viscosity is achieved by keeping the polymer mixture at a temperature above the freezing point of the polymer, but below room temperature. Preferably, the polymer mixture and blood are allowed to stand undisturbed for a sufficient amount of time to allow more complete precipitation of the proteins present in the blood. Most preferably, the polymer mixture is maintained at a temperature of 4° C. and the combination of polymer mixture and blood is allowed to precipitate for approximately 20 minutes at 4° C.

The supernatant retains the albumin fraction while the precipitate contains the immunoglobulin fraction.

Albumin is precipitated from the supernatant by the addition of a sufficient amount of a zinc compound, most preferably zinc sulfate heptahydrate.

Immunoassay

It will be understood by those skilled in the art that the biomolecule isolation method described above can be used in an immunoassay for detection of specific antibodies in a biological sample. Antigen is mixed with a biological sample containing antibodies specific for the antigen, and the mixture is incubated for a sufficient amount of time to create antibody-antigen conjugates. Isolation of the antibody-antigen conjugates from free antigen is achieved in a manner similar to the above-described immunoglobulin isolation method.

Biological Fluids

It will be understood by those skilled in the art that the methods provided herein are useful in isolating biomolecules from biological fluids other than blood serum including blood plasma, urine, spinal fluid, fermentation fluid, lymph fluid, tissue culture fluid and ascites fluid.

Isolation of Proteins from Urine and Spinal Fluid

In an alternate preferred method, proteins are isolated from urine or spinal fluid by precipitation with a solution containing a soluble, linear polymer adjusted to a predetermined pH with glycine. Most preferably, a mixture of polyvinylpyrrolidone and polyethylene glycol is combined with a solution of zinc glycinate and the combined solution is added to the urine or spinal fluid sample to create a precipitate containing the proteins.

Biomolecule Isolation Kit

A kit for the isolation of a biomolecule from a biological sample is provided wherein the kit contains a soluble, linear polymer or mixture of polymers. Preferably, the polymer is a mixture of polyvinylpyrrolidone and polyethylene glycol for the isolation of proteins, most preferably immunoglobulins, from a biological sample such as a human blood serum sample. Preferably, the polymer is preadjusted to a pH that will provide optimal separation of the biomolecule of interest from the other components in the sample.

If the biomolecule of interest is to be isolated in the precipitate formed by combining the sample with the polymer, then the kit can additionally contain a resuspension solution for redissolving the precipitate. Preferably, the resuspension solution is an alkaline solution for stable resuspension of the precipitate.

The protein isolation methods described above will be further understood with reference to the following non-limiting examples.

Example 1

Effect of pH on Isolation of Immunoglobulins from Human Serum with a Polymer Mixture of PVP and PEG Immunoglobulins were isolated from human serum with a polymer mixture of PVP (MW=40,000) and PEG (MW=3500). A 20% solution of each polymer, obtained from Sigma, St. Louis, Mo., was prepared by adding 20 grams of polymer to 100 ml of either 10X phosphate buffered saline (PBS), 1X PBS, or distilled water.

The pH of each 20% polymer solution was adjusted to a pH of approximately 7 with an amino acid solution containing 1.1 g/ml glycine hydrochloride, 1.21 g/ml cysteine and 1.46 g/ml lysine in water. Each amino acid was obtained from Sigma (St. Louis, Mo.). The final concentration of amino acids in the polymer solution was 10 mM.

Ten milliliters of the pH-adjusted polymer solution was added to 1.25 ml of human serum. The volume of aqueous PVP or PEG added to each sample is set forth below in Table I.

TABLE I

| | Amount of PVP and PEG added to Protein Samples | |
|---|---|---|
| Sample | 20% PVP in Water | 20% PEG in Water |
| 1 | 5 ml | 5 ml |
| 2 | 10 ml | 0 ml |
| 3 | 9 ml | 1 ml |
| 4 | 8 ml | 2 ml |
| 5 | 7 ml | 3 ml |
| 6 | 6 ml | 4 ml |
| 7 | 5 ml | 5 ml |
| 8 | 4 ml | 6 ml |
| 9 | 3 ml | 7 ml |
| 10 | 2 ml | 8 ml |
| 11 | 1 ml | 9 ml |
| 12 | 0 ml | 10 ml |

The volume of polymer dissolved in either 10X PBS, 1X PBS, or water is set forth below in Table II.

TABLE II

| | Volume of Polymer Dissolved in Solution | | |
|---|---|---|---|
| Sample | Polymer in 10X PBS | Polymer in 1X PBS | Polymer in H₂O |
| A | 10.0 ml | 0.0 ml | 0.0 ml |
| B | 5.0 ml | 5.0 ml | 0.0 ml |
| C | 2.5 ml | 7.5 ml | 0.0 ml |
| D | 1.0 ml | 9.0 ml | 0.0 ml |
| E | 0.0 ml | 5.0 ml | 5.0 ml |
| F | 0.0 ml | 2.5 ml | 7.5 ml |
| G | 0.0 ml | 1.0 ml | 9.0 ml |
| H | 0.0 ml | 0.0 ml | 10.0 ml |

Both sets of samples were incubated at 4° C. for 18 hours. A precipitate formed. The supernatant was removed from the precipitate by decantation. The precipitate was redissolved in phosphate buffered saline. Both the precipitate and the supernatant for each sample were run on a two-dimensional agarose electrophoretic gel for 18 hours. The electrophoretic gel showed good separation of globulin and albumin.

A 3 µl aliquot of the redissolved precipitate from each sample was loaded into wells and migrated on the left portion of the gel. A 3 µl aliquot of the supernatant from each sample was loaded into wells and migrated on the right portion of the gel. Serum proteins were detected by precipitation with a whole molecule anti-human serum antibody (Sigma, St. Louis, Mo.). Immunoglobulins were detected by precipitation with an anti-human whole IgG antibody (Sigma, St. Louis, Mo.). Precipitates were stained with the protein assay reagent Coomassie Blue. (Pierce Chemical Co., Rockford, Ill.)

The amount of globulin in the precipitate was maximized in samples 9–12, G and H. These samples, especially samples 9–10, also had virtually no globulin in the supernatant.

Example 2

Precipitation of Proteins from Human Urine with a Polymer Mixture of PVP and PEG and Zinc Glycinate The following three experiments were conducted to compare the ability of a solution containing polyvinylpyrrolidone (PVP, 40,000 MW), polyethylene glycol (PEG, 3,350 MW), and zinc glycinate with the ability of a solution containing deionized water and zinc glycinate to precipitate proteins from urine or spinal fluid.

Experiment 2A

A 28% solution of each polymer was prepared by adding 14 grams of polymer, obtained from Sigma, St. Louis, Mo., to 100 ml of distilled water. Equal volumes of each polymer were combined to form a PVPPEG mixture. The pH of the PVP/PEG mixture was 3.6.

A solution of zinc glycinate was prepared by reacting 1M glycine with 0.4M zinc oxide in deionized water.

One volume of the zinc glycinate solution was combined with nine volumes of the PVP/PEG mixture. As a control, one volume of the zinc glycinate solution was combined with nine volumes of deionized water to create a 1:10 dilution.

As shown below in Table III, various aliquots of the PVP/PEG and zinc glycinate mixture (PVP/PEG/ZnGly), or the control mixture (dH₂O/ZnGly), were added to 1 ml of human urine and the amount of precipitate formed in each tube was compared visually.

TABLE III

Effect of Volume of PVP/PEG/ZnGly (pH 3.6) or dH₂O/ZnGly on Protein Precipitation from Urine

| Volume Added | Precipitate Formed | |
|---|---|---|
| | PVP/PEG/ZnGly | dH₂O/ZnGly |
| 100 µl | 2.0 X | 1.0 X |
| 200 µl | 4.0 X | 1.0 X |
| 300 µl | 4.5 X | 1.5 X |
| 400 µl | 5.0 X | 2.5 X |
| 500 µl | 5.5 X | 2.5 X |
| 600 µl | 6.0 X | 2.5 X |
| 700 µl | 6.0 X | 2.5 X |
| 800 µl | 6.0 X | 2.5 X |
| 900 µl | 6.0 X | 2.5 X |
| 1000 µl | 6.0 X | 2.5 X |

The results show that the amount of protein precipitated from urine by the PVP/PEG/zinc glycinate solution was greater than the amount precipitated by an equal volume of the dH₂O/zinc glycinate solution.

Experiment 2B

Solutions containing PVP/PEG/zinc glycinate and dH₂O/zinc glycinate were prepared as described in Experiment 2A above. The pH of each solution was adjusted to a more neutral pH with a solution of glycine hydrochloride (500 mg glycine HCl in 10 ml deionized water). A 1.2 ml aliquot of glycine hydrochloride was added to the PVP/PEG/zinc glycinate solution to raise the pH to 6.2. A 2.2 ml aliquot of glycine hydrochloride was added to the dH₂O/zinc glycinate solution to raise the pH to 6.4.

As shown below in Table IV, various aliquots of the PVP/PEG/zinc glycinate mixture (PVP/PEG/ZnGly), or the control mixture (dH₂O/ZnGly), were added to 1 ml of human urine and the amount of precipitate formed in each tube was compared visually.

TABLE IV

Effect of Volume of PVP/PEG/ZnGly (pH 6.2) or dH₂O/ZnGly (pH 6.4) on Protein Precipitation from Urine

| Volume Added | Precipitate Formed | |
|---|---|---|
| | PVP/PEG/ZnGly | dH₂O/ZnGly |
| 200 µl | 3.0 X | 1.0 X |
| 400 µl | 5.0 X | 2.0 X |
| 600 µl | 6.0 X | 4.0 X |
| 800 µl | 8.0 X | 8.0 X |
| 1000 µl | 8.0 X | 8.0 X |

The results show that the amount of protein precipitated from urine by the PVP/PEG/zinc glycinate solution was greater than the amount precipitated by an equal volume of the dH₂O/zinc glycinate solution at volumes less than 800 µl. In addition, the adjustment of the pH to 6.2 increased the amount of precipitation caused by addition of the PVP/PEG/zinc glycinate mixture when larger volumes were added.

Experiment 2C

Solutions containing PVP/PEG/zinc glycinate and dH$_2$O/zinc glycinate were prepared and pH adjusted as described in Experiment 2B above.

As shown below in Table IV, various aliquots of the PVP/PEG/zinc glycinate mixture (PVP/PEG/ZnGly), or 500 µl of the control mixture (dH$_2$O/ZnGly), were added to 1 ml of human cerebral spinal fluid, the mixtures were incubated at 20° C. for thirty minutes, and the amount of precipitate formed in each tube was compared visually.

TABLE V

Effect of Volume of PVP/PEG/ZnGly on Protein Precipitation from Spinal Fluid

| Volume Added | Precipitate Formed |
|---|---|
| 100 µl | 0.3 X |
| 200 µl | 1.0 X |
| 300 µl | 2.0 X |
| 400 µl | 3.0 X |
| 500 µl | 5.0 X |
| control | 0.0 X |

The results show that increasing amounts of protein were precipitated from spinal fluid with the addition of increasing quantities of the PVP/PEG/zinc glycinate solution. In contrast, the dH$_2$O/zinc glycinate solution failed to produce a visible protein precipitate.

Example 3

Precipitation of Gammaglobulins from Mouse Ascites Fluid at 4° C.

The following experiment was conducted to determine the effect of temperature on precipitation of gammaglobulins from mouse ascites fluid with a solution containing polyvinylpyrrolidone (PVP, 40,000 MW) and polyethylene glycol (PEG, 3,350 MW)

A 28% solution of each polymer was prepared by adding 28 grams of polymer, obtained from Sigma, St. Louis, Mo., to 100 ml of 0.1M sodium acetate. Equal volumes of each polymer solution were combined to form a PVPPEG mixture. The pH of the PVP/PEG mixture was adjusted to 5.8 with glacial acetic acid.

Mouse ascites fluid (0.5 ml) was combined with 2.0 ml of the PVP/PEG mixture under each of the following reaction conditions:

Reaction 1—Precipitation reaction was conducted at 20° C. After precipitation, mixture was immediately centrifuged.

Reaction 2—Precipitation reaction was conducted at 4° C. After precipitation, mixture was immediately centrifuged.

Reaction 3—Precipitation reaction was conducted at 20° C. After precipitation, mixture was allowed to stand for 30 minutes at 20° C. prior to centrifugation.

Reaction 4—Precipitation reaction was conducted at 4° C. After precipitation, mixture was allowed to stand for 30 minutes at 4° C. prior to centrifugation.

Centrifugation was performed at 20° C. for 30 minutes at 4500 rpm. The supernatant was decanted and the precipitate resuspended in a resuspension buffer. The results were as follows:

TABLE VI

Effect of Temperature on Protein Precipitation from Ascites Fluid

| Reaction Number | Precipitate Color | Precipitate Volume | Supernatant Clarity |
|---|---|---|---|
| 1 | off-white | 1.0 X | cloudy |
| 2 | brown | 1.5 X | clear |
| 3 | off-white | 1.0 X | clear |
| 4 | brown | 2.0 X | clear |

A 3 µl aliquot of the redissolved precipitate from each reaction was loaded into wells and migrated on an agarose electrophoretic gel. A 3 µl aliquot of the supernatant from each reaction was loaded into wells and migrated on a second agarose electrophoretic gel. Gammaglobulin was detected by precipitation with an anti-mouse whole IgG antibody (Sigma, St. Louis, Mo.). Precipitates were stained with the protein assay reagent Coomassie Blue. (Pierce Chemical Co., Rockford, Ill.)

The results of the electrophoretic gels showed that Reactions 2 and 4 contained more gammaglobulin in the precipitates than Reactions 1 and 3. Reactions 2 and 4 also contained less gammaglobulin in the supernatants than Reactions 1 and 3. Reaction 4 had the greatest amount of gammaglobulin in the precipitate and the least amount of gammaglobulin in the supernatant. The amount of other proteins in the supernatants each of the four reactions was far greater than the amount in each of the four precipitates.

The results indicate that a polymer mixture having a greater viscosity has a greater ability to isolate gammaglobulin in the precipitate. The PVP/PEG polymer mixture has a greater viscosity at 4° C. than at 20° C.

Example 4

Precipitation of Proteins from Blood after Adjustment of pH of PVP/PEG Solution with Imidazole and 6-Amino Caproic Acid The following experiments were conducted to determine the pH stability of a PVP/PEG solution containing imidazole and 6-amino caproic acid.

Experiment 4A

A polymer solution containing 14% each PVP and PEG, prepared as described above in Example 3, was adjusted to pH 7.2 with 6-amino caproic acid and imidazole. The final solution (50 ml PVP/PEG) contained 2.1% 6-amino caproic acid and 100 mg imidazole.

A 0.5 ml aliquot of goat serum, chilled to 2° C., was reacted with 2.0 ml, 3.0 ml, 4.0 ml, and 5.0 ml of the PVP/PEG polymer solution, pH 7.2, by vortexing briefly and then allowing the reactants to stand at 2° C. for 20 minutes. Reactions were then centrifuged at 20° C. for 30 minutes at 4500 rpm. The supernatant was decanted, the amount of precipitate observed visually, and the precipitate resuspended in 2.0 ml of a resuspension buffer. The results were as follows:

As the volume of the PVP/PEG polymer solution added to the serum increased, the amount of precipitate observed increased. In addition, the pH of the PVP/PEG polymer solution remained constant over time.

Experiment 4B

The pH of a polymer solution containing 14% each PVP and PEG was adjusted as described above in Experiment 4A.

A 5.0 ml aliquot of goat serum, chilled to 4° C., was reacted with 20 ml, and 40 ml of the PVP/PEG polymer solution, pH 7.2, by vortexing briefly and then allowing the reactants to stand at 4° C. for 20 minutes. Reactions were then centrifuged at 20° C. for 30 minutes at 4500 rpm. The supernatant was decanted and the precipitates observed visually. The supernatants appeared clear. The precipitate in the reaction containing 40 ml of the PVP/PEG polymer solution contained slightly more precipitate than the reaction containing 20 ml of the PVP/PEG solution.

Both precipitates were resuspended in 1 ml of chilled (4° C.) sodium bicarbonate resuspension buffer.

A second precipitation was performed by adding 2.0 ml of a chilled (2° C.) PVP/PEG polymer solution that had been adjusted to a pH of 6.2 with 6-amino caproic acid to each resuspended precipitate. The mixture was vortexed briefly and allowed to stand at 2° C. for 30 minutes. Centrifugation and decantation of supernatants was performed as described above. Both supernatants appeared clear. Both precipitates had one third less precipitate and appeared lighter in color than in the first precipitate.

Example 5

Effect of Tween-20™ on Precipitation of Proteins from Ascites Fluid

The following experiment was conducted to demonstrate the effect of the adding the detergent polyoxyethylenesorbitan (Tween-20™) to ascites fluid prior to precipitation with a PVP/PEG solution.

A PVP/PEG polymer solution (21% of each polymer) was prepared as described above in Example 3. The pH of the polymer solution was adjusted to pH 7.0 with imidazole.

A 4.7% Tween-20™ (Sigma Chemical Company, St. Louis, Mo.) solution was made up in deionized water by dissolving 0.5 ml Tween-20™ in 10 ml deionized water. Further dilutions of the 4.7% solution were made with deionized water to yield 0.94%, 1.88%, 2.82%, and 3.76% concentrations.

One milliliter of each of the above Tween-20™ solutions were added to 1.0 ml mouse ascites fluid. One milliliter of deionized water was added to 1.0 ml ascites fluid as a control. All samples were mixed well and allowed to stand for 15 minutes at 20° C.

Two milliliters of the PVP/PEG polymer solution were then added to each sample while vortexing. All samples were mixed for 15 minutes at 20° C. The reactants were then centrifuged at 20° C. for 30 minutes at 4500 rpm, supernatant decanted, and the precipitates resuspended in 1.0 ml sodium bicarbonate buffer.

One milliliter of the PVP/PEG polymer solution was added to the resuspended precipitate while vortexing. All samples were mixed for 15 minutes at 20° C., centrifuged, supernatants decanted, and precipitates resuspended as described above.

Each sample was run on both agarose gel and rocket electrophoresis. The percent of gammaglobulin in each of four fractions for each sample was calculated. The results are shown in Table VII.

TABLE VII

Effect of Detergent Concentration on Protein Precipitation from Ascites Fluid

| Reaction Number | Tween-20 ™ Percent | % gammaglobulin per fraction | | | |
|---|---|---|---|---|---|
| | | 1 | 2 | 3 | 4 |
| 1 | 0 | 6.7 | 63.0 | 19.5 | 10.8 |
| 2 | 0.94 | 3.6 | 70.1 | 17.9 | 8.4 |
| 3 | 1.88 | 2.7 | 74.8 | 15.7 | 6.8 |
| 4 | 2.82 | 1.6 | 78.7 | 13.7 | 6.0 |
| 5 | 3.76 | 2.1 | 78.0 | 13.9 | 6.0 |

The results indicated that, as the percent of Tween-20™ increased, the purity of gammaglobulin in the precipitate increased. No albumin was detected in reaction numbers 3, 4 or 5, containing 1.88%, 2.82% or 3.76% Tween-20™. Therefore, when Tween-20™ was added to the sample prior to precipitation with the PVP/PEG solution, protein complexes in the sample became dispersed, allowing for a purer gammaglobulin fraction to be precipitated by the polymer solution.

Example 6

Effect of Preincubation with Brij 35™ and Triton X-102™ on Precipitation of Proteins from Human Plasma The following experiment was conducted to demonstrate the effect of the adding the polyoxyethylene ethers Brij 35™ and Triton X-102™ (two commercially available biological detergents) to human plasma prior to precipitation with two different PVP/PEG solutions.

A PVP/PEG polymer solution (20% of each polymer) was prepared as described above in Example 3. The pH of the polymer solution was adjusted to pH 5.8 with 6-amino caproic acid and imidazole. A second PVP/PEG polymer solution containing 6.6% of each polymer and 33% ethanol was also prepared. Ethanol is routinely added to blood samples for inactivation of contaminating virus.

A 1% Triton X-102™ solution and a 15% Brij 35™ solution (both from Sigma Chemical Company, St. Louis, Mo.) were made up in deionized water and the Brij 35™ solution was further diluted with the 1% Triton X-102™ solution to obtain 15%, 7.5%, 3.75%, 1.9%, 0.9% and 0.5% concentrations of Brij 35™.

One milliliter of each of the above Triton X 102™/Brij 35™ solutions were added to 1.0 ml human plasma, mixed well and allowed to stand for 35 minutes at 20° C.

Two milliliters of the 20% PVP/PEG polymer solution were then added to each sample while vortexing. All samples were mixed for 15 minutes at 20° C. The reactants were then centrifuged at 20° C. for 30 minutes at 3600 rpm, supernatant decanted, and the precipitates resuspended in 1.0 ml deionized water. A 200 µl aliquot of each resuspended precipitate was removed for analysis.

A 400 µl aliquot was removed from the remaining 800 µl and placed in a clean centrifuge tube, referred to in this experiment as Group I. The remaining 400 µl sample is referred to in this experiment as Group II. A 1.2 ml aliquot of the 6.6% PVP/PEG solution (containing ethanol) was added to the tubes in Group I. A 0.4 ml aliquot of the 20% PVP/PEG solution was added to the tubes in Group II. The tubes in both groups were mixed for 30 minutes at 20° C., centrifuged as described above, supernatants decanted, and precipitates resuspended in 0.4 ml sodium bicarbonate buffer.

Each sample was analyzed by protein cellulose acetate electrophoresis. In both groups, as the percentage of Brij 35™ decreased, the amounts of albumin, beta and alpha globulins also decreased. However, the amount of gammaglobulin in the resuspended precipitate increased.

Each sample was assayed for the presence of fibrinogen by adding 25 µl of reconstituted thrombin to a 200 µl aliquot of each resuspended precipitate from Groups I and II. The results are shown below in Table VIII.

TABLE VIII

Effect of Brij 35 ™ Concentration on
Fibrinogen Contamination of Gammaglobulin
Precipitated from Human Plasma

| Reaction Number | Brij 35 ™ Percent | Fibrinogen concentration |
| --- | --- | --- |
| Group I | | |
| control | 0 | ++++ |
| 1 | 15.0% | ++++ |
| 2 | 7.5% | +++ |
| 3 | 3.75% | ++ |
| 4 | 1.9% | +(trace) |
| 5 | 0.9% | − |
| 6 | 0.5% | − |
| Group II | | − |

The results indicated that, when using a PVP/PEG polymer solution in the presence of ethanol, to inactivate viruses, the amount of Brij 35™ should be no greater than 1% to prevent contamination of the gammaglobulin precipitate by fibrinogen.

Example 7

Effect of Sodium Dodecyl Sulfate on Precipitation of Proteins from Ascites Fluid The following experiment was conducted to demonstrate the effect of the adding the detergent sodium dodecyl sulfate (SDS) to a PVP/PEG solution for subsequent precipitation of gammaglobulins from ascites fluid.

A PVP/PEG polymer solution (21% of each polymer) was prepared as described above in Example 3. The pH of the polymer solution was adjusted to pH 6.5 with imidazole. SDS was added to tubes containing the PVP/PEG solution so that the solutions contained varying concentrations of SDS ranging from 1.0 to 0 percent.

A 0.5 ml aliquot of a 2% Triton X-100™ (Sigma Chemical Company, St. Louis, Mo.) solution was added to 0.5 ml mouse ascites fluid, mixed well and allowed to stand for 15 minutes at 20° C.

One milliliter of each PVP/PEG/SDS solution was added to each sample while vortexing. The reactions were mixed for 30 minutes at 20° C., centrifuged at 3600 rpm at 20° C. for 30 minutes, supernatants decanted, and precipitates resuspended in 0.5 ml deionized water.

A 0.5 ml aliquot of a PVP/PEG solution without SDS was then added to each resuspended precipitate while vortexing, mixed 30 minutes at 20° C., centrifuged as above, supernatants decanted, and precipitates resuspended in 0.5 ml sodium bicarbonate buffer.

The resuspended precipitates were subjected to rocket electrophoresis. The results indicated that, as the amount of SDS in the PVP/PEG polymer solution increased, the amount of total proteins in the final precipitate decreased, but the amount of gammaglobulin remained constant, indicating that the presence of SDS enhanced the purity of the precipitated gammaglobulin because there was less alpha and beta globulin contamination.

Example 8

Comparative Study of the Precipitation of
Monoclonal Antibodies from Ascites Fluid with
PEG and a PVP/PEG Polymer Mixture The following experiment was conducted to compare the amount and purity of monoclonal antibodies precipitated from mouse ascites fluid with a polymer solution of PEG or a polymer mixture of PVP/PEG.

A PVP/PEG polymer solution (20% of each polymer) was prepared as described above in Example 3. A 20% PEG (MW 8000) polymer solution was similarly prepared. The pH of each polymer solution was adjusted to pH 6.6 with imidazole.

One milliliter of ascites fluid was preincubated with either 1.0 ml deionized water (Reaction 1), 1.0 ml 2% Triton X-102™ (Reaction 2), or 1.0 ml 1.8% Triton X-102™/3% Brij 35™ (Reaction 3). Each of these three reactions was mixed well and allowed to stand at 20° C. for 15 minutes.

Either 2.0 milliliters of the PVP/PEG solution (Group I) or the PEG solution (Group II) was added to each of the preincubation mixtures. Both groups were mixed for 30 minutes at 20° C., centrifuged at 4000 rpm for 30 minutes at 20° C., supernatants decanted, and precipitates resuspended in 1.0 ml deionized water.

One milliliter of the PVP/PEG solution was added to Reactions 2 and 3 of Group I while vortexing (Reaction 1 did not centrifuge). One milliliter of the PEG solution was added to Reactions 1–3 of Group II while vortexing. Both groups were mixed for 30 minutes at 30° C., centrifuged as described above, supernatants decanted, and precipitates resuspended in 1 ml sodium bicarbonate.

The following observations were noted. The reactions in the Group II series (precipitated with PEG) had larger first precipitates compared with the respective reactions in the Group I series (precipitated with PVP/PEG). The reactions in the Group II series (PEG) had cloudy supernatants, indicating that not all protein was able to be centrifuged to the bottom of the tube. Reactions 2 and 3 in Group I (PVP/PEG) had clear supernatants whereas the supernatants from the same reactions in Group II were very cloudy.

The samples were analyzed by agarose gel protein electrophoresis. The results showed the Group II (PEG) series to have more albumin, beta globulin, and other contaminating proteins in the first precipitates than in the first precipitates obtained from Group I (PVP/PEG).

Example 9

Effects of pH on Solubility of Gammaglobulin
Precipitated from Sera with a PVP/PEG Polymer
Solution The following experiment was conducted to determine the whether the pH of the resuspension solution has an effect on the sglubility and stability of gammaglobulin precipitated from sera with a PVP/PEG polymer solution.

Experiment 9A

A one milliliter sample of goat serum or rabbit serum (Sigma Chemical Company, St. Louis, Mo.) was preincubated with 1.0 ml 2% Triton X-102™ (Sigma), mixed well and allowed to stand for 15 minutes at 20° C.

A PVP/PEG polymer solution (20% of each polymer) was prepared as described above in Example 3. The pH of each polymer solution was adjusted to pH 6.6 with imidazole.

A 2.0 ml aliquot of the PVP/PEG solution was added to each preincubated sample while vortexing, mixed 30 minutes at 20° C., centrifuged at 3600 rpm for 30 minutes at 20° C., supernatants were decanted, and the precipitates resuspended in 1 ml of a solution containing 5 ml of 0.5M imidazole in deionized water solution and 5 ml of glycerol, pH 9.4 (Aldrich Chemical Company, Milwaukee, Wis.). The resuspended precipitates were allowed to stand for 10 minutes at 20° C.

A 1.0 ml aliquot of the PVP/PEG polymer solution was added to each tube while vortexing and tubes were mixed, centrifuged, and supernatants decanted as described above. The precipitates were resuspended in 1.0 ml of deionized water and the second precipitation step was repeated. The resulting precipitates were resuspended in 250 µl, 500 µl, 750 µl or 1000 µl of a 50/50 solution of glycerol and 0.06M sodium bicarbonate, pH 8.2.

The results indicated that, when either goat or rabbit gammaglobulin precipitates were resuspended in an alkaline solution, the precipitates are readily dissolved and are clearer than when resuspended in a neutral or acid solution.

Experiment 9B

Ten test tubes containing 0.5 ml human plasma were incubated for 15 minutes with 2% Triton X-102™ in deionized water as described above. Following incubation, one milliliter of the PVP/PEG polymer solution (20% of each polymer) described above was added to each preincubated sample while vortexing, mixed 30 minutes at 20° C., centrifuged at 2500 rpm for 30 minutes at 20° C., supernatants were decanted, and the protein precipitates resuspended in 0.5 ml of a 0.5M imidazole solution at each of the following pH values: (pH was adjusted with glacial acetic acid)

TABLE IX

| pH of Imidazole Resuspension Solution | |
|---|---|
| Reaction No. | pH |
| 1 | 10.4 |
| 2 | 9.2 |
| 3 | 8.5 |
| 4 | 8.0 |
| 5 | 7.0 |
| 6 | 6.4 |
| 7 | 5.8 |
| 8 | 5.0 |
| 9 | 4.4 |

The pH gradient displayed a clear relationship between pH and clarity of resuspended gammaglobulin. With each drop in pH, there was an increase in the cloudiness of the sample. Sample 1 at pH 10.4 was clear. The samples remained fairly clear, with an increase in cloudiness accompanying each pH drop, up to sample 5 at pH 7.0. At pH 6.4, the sample was opaque. In samples 8 and 9, the gammaglobulin precipitated out of solution.

The results indicated that the pH of the gammaglobulin resuspension solution is directly proportional to the clarity of the resuspension with alkaline pH clearly favored.

Experiment 9C

Ten test tubes containing 1.0 ml human plasma were incubated for 15 minutes with 2% Triton X-102™ in deionized water as described above. Following incubation, two milliliters of the PVP/PEG polymer solution (20% of each polymer) described above was added to each preincubated sample while vortexing, mixed 30 minutes at 20° C., centrifuged at 3600 rpm for 30 minutes at 20° C., supernatants were decanted, and the protein precipitates resuspended in 1.0 ml of a Trizma™ base solution prepared as follows.

A 0.1M solution of Trizma™ base (Sigma Chemical Company, St. Louis, Mo.) was prepared. A pH gradient was established by adjusting the pH of the Tris™ solution with concentrated glacial acetic acid. The following pH values were analyzed for their ability to resuspend the protein precipitates containing gammaglobulin.

TABLE X

| pH of Tris ™ Resuspension Solution | |
|---|---|
| Reaction No. | pH |
| 1 | 10.4 |
| 2 | 9.4 |
| 3 | 8.5 |
| 4 | 8.0 |
| 5 | 7.4 |
| 6 | 7.0 |
| 7 | 6.5 |
| 8 | 5.9 |
| 9 | 4.2 |

As was seen with the imidazole experiment (Experiment 9B above), the pH gradient displayed a clear relationship between pH and clarity of protein suspension. Clarity was greatest at alkaline pH values and diminished with each subsequent drop in pH. However, the samples resuspended in the imidazole solutions (Experiment 9B) were clearer overall that the samples resuspended in the Tris™ solutions. The precipitate resuspended at pH 10.4 was fairly clear, but clarity dropped to mostly cloudy by pH 8.0. The sample at pH 7.0 contained apparent precipitation. The protein precipitate of samples 8 and 9 did not resuspend. After standing overnight at 4° C., precipitation was apparent in all samples resuspended in a solution having a pH lower than pH 7.4

The results again indicated that the protein resuspension solution should be alkaline for stable and complete resuspension of the protein precipitated by the polymer solution.

Modifications and variations of the present biomolecule isolation method will be obvious to those skilled in the art from the foregoing detailed description of the invention. Such modifications and variations are intended to come within the scope of the appended claims.

I claim:

1. A method of isolating at least one biomolecule from a biological sample comprising the steps of:

a) adding a sufficient amount of a solution of at least two soluble, linear polymers to a biological sample solution to form a precipitate, wherein a first polymer is polyvinylpyrrolidone and a second polymer is selected from the group consisting of polyethylene glycol, dextran, nonylphenol-ethoxylates, polyvinyl alcohol, and mixtures thereof, and adjusting the solution to a predetermined pH; and b) separating the solution into two fractions, a supernatant and a precipitate, wherein the biomolecule is isolated from either the supernatant or precipitate.

2. The method of claim 1 wherein the pH is adjusted with a low molecular weight moiety containing an amino or carboxyl group.

3. The method of claim 2 wherein the low molecular weight moiety is selected from the group consisting of imidazole, amino caproic acid, an amino acid and mixtures thereof.

4. The method of claim 1 wherein the second polymer is polyethylene glycol and the polyvinylpyrrolidone is first mixed with the polyethylene glycol and the polymer mixture is added to the sample.

5. The method of claim 4 wherein the polyvinylpyrrolidone has a molecular weight of approximately 40,000 and the polyethylene glycol has a molecular weight of approximately 3500.

6. The method of claim 1 wherein the biomolecule is selected from the group consisting of a protein, carbohydrate, non-protein hormone, and nucleic acid.

7. The method of claim 6 wherein the protein is an immunoglobulin.

8. An assay for determining the albumin to globulin ratio in plasma comprising the steps of:
   a) adding a sufficient amount of a polymer solution of polyvinylpyrrolidone and polyethylene glycol to the plasma to precipitate the globulin, leaving the albumin in the supernatant, wherein the pH of the plasma is adjusted to an approximately neutral pH;
   b) separating the precipitate from the supernatant;
   c) measuring the concentrations of globulin and albumin; and
   d) calculating the ratio of albumin to globulin.

9. A method for determining the disposition of a drug in serum proteins comprising the steps of:
   a) adding a sufficient amount of an aqueous solution of polyvinylpyrrolidone and polyethylene glycol to serum to precipitate the globulin, and adjusting the pH of the serum to a predetermined value;
   b) separating the solution into two fractions, a supernatant fraction and a precipitate fraction wherein the globulin-bound drug is isolated from the precipitate fraction and the albumin-bound drug is isolated from the supernatant fraction; and
   c) analyzing the precipitate and supernatant fractions to detect the drug.

10. A method for dissolving a protein, precipitated from a biological sample, comprising:
    a) adding a sufficient amount of a solution of at least two soluble, linear polymers to a biological sample solution to form a precipitate, wherein a first polymer is polyvinylpyrrolidone and a second polymer is selected from the group consisting of polyethylene glycol, dextran, nonylphenol-ethoxylates, polyvinyl alcohol, and mixtures thereof; and adjusting the solution to a predetermined pH;
    b) separating the solution into two fractions, a supernatant and a precipitate, wherein the biomolecule is isolated from the precipitate; and
    c) dissolving the precipitated protein in an aqueous alkaline solution.

11. The method of claim 10 wherein the aqueous alkaline solution is selected from the group consisting of glycerol, sodium bicarbonate, imidazole, an alkaline salt solution, tris[hydroxymethyl] aminomethane, and mixtures thereof.

* * * * *